Jan. 27, 1970 G. MERRILL Plant Pat. 2,964
PEACH TREE
Filed May 17, 1968
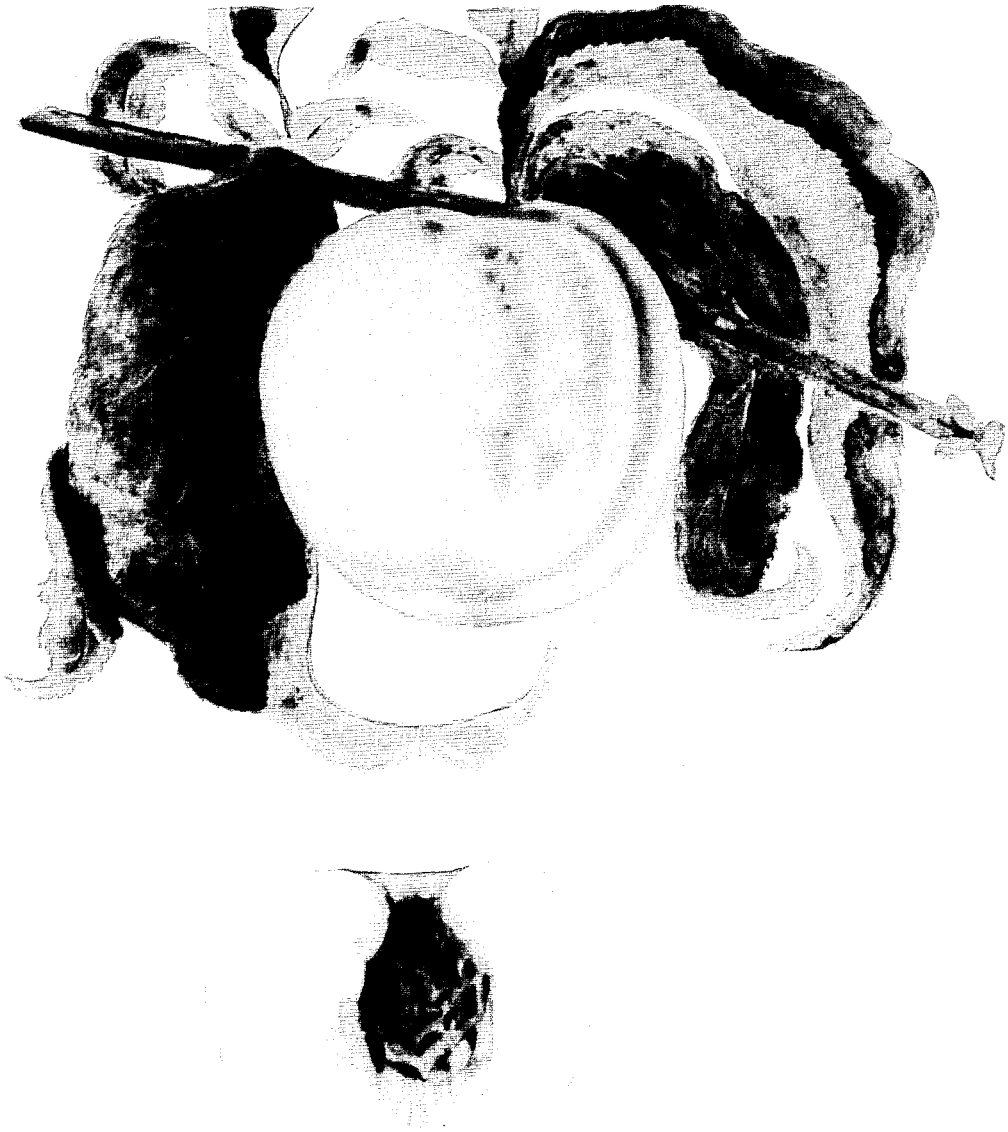
GRANT MERRILL
INVENTOR
Virgil L. Gerard
ATTORNEYS United States Patent Office Plant Pat. 2,964
Patented Jan. 27, 1970

2,964

PEACH TREE

Grant Merrill, Tulare County, Calif.
(416 N. Anderson Road, Exeter, Calif. 93221)

Filed May 17, 1968, Ser. No. 730,208
Int. Cl. A01h 5/08
U.S. Cl. Plt.—43 1 Claim The present invention relates to a peach tree and more particularly to a new and distinct variety thereof, broadly characterized by its uniformly very firm flesh and the bright undercolor of its skin which is covered by a red blush covering about half the surface of fruit exposed to the sun, and by an extremely short pubescence.

The instant variety most nearly resembles the Improved Pacifica (U.S. Plant Patent No. 2,425) but is an improvement thereon in having a brighter undercolor on the skin, a shorter pubescence, and flesh which is uniformly firm as contrasted with the flesh of the Improved Pacifica which is firmer near the outside, and softer inside.

I originated this variety by planting seeds of the Merrill Bonanza peach at Red Bluff, Calif. The pollen parent was presumed to be a nectarine as determined by planting seeds from open pollinated blossoms of the instant variety and observing that about one-fourth of the resulting trees bore nectarines. The instant variety asexually reproduced was budded to seedlings of Nemaguard peach trees at Exeter, Tulare County, Calif., and the resulting tree and fruit characteristics from such budding proved identical to the original tree.

The accompanying drawing is an oil painting of a characteristic twig of the subject peach tree bearing foliage and a mature fruit, and additionally, showing a fruit of the subject variety divided on its suture plane to reveal flesh coloration and stone characteristics.

Referring more specifically to the pomological characteristics of this new and distinct variety of peach tree, the following has been observed under the ecological conditions prevailing at Exeter, Tulare County, Calif., and is an outline description thereof. All major color plate identification are by reference to Maerz and Paul, Dictionary of Color, first edition.

TREE

General: Large, vigorous, productive, regular bearer, shaped by pruning, usually into a vase shaped tree.

Trunk: Medium size, medium shaggy, gray, lenticels medium in size and quantity.

Leaves: Medium size and shape, averaging 1¼ to 1¾ inches in width and 5¾ to 7½ inches long; shape—lanceolate; tip—accuminate, medium thick; color of upper surface—light green 13–L–1; surface—smooth on young leaves, rugose on older leaves; margin—crenate; petiole—medium length; deciduous.

Glands: Two to eight in number averaging three, and positioned at the base of the leaf and on the upper length of the petiole; stipules at the base of the leaf dropping off early as the leaf grew.

FLOWER BUDS

Medium size, round, free, pubescent.

FLOWERS

Midseason, first blooming Feb. 24, 1968; a year of early blooming, full bloom Mar. 3, 1968; pink in color, large and showy, pollen moderate in amount.

FRUIT

Size: Variable, generally medium in size; axial measurement, 2½ to 3 inches; transverse in suture plane, 2½–3 inches; at right angle to suture plane, 2⅜ to 2⅞ inches.

Form: Generally globose.

Suture: A distinct shallow line extending from base to beyond and discontinuous at apex, with slight depression beyond the pistil point.

Ventral surface: Rounded, slight lips usually unequal.

Cavity: Oval, elongated in a suture plane, with suture showing strongly on one side, slightly on the other side; yellow, usually with red markings; ⅜ to ½ inch deep, ¾ to 1⅛ inches wide.

Base: Usually slightly truncate.

Apex: Rounded with slight tip on most, none to as long as ⅛ inch in length.

Stem: Frequently adhering to flesh, ⅛ to ¼ inch long, ⅛ inch in diameter.

Skin: Medium thin, medium tender, tenacious to flesh unless very ripe, pubescence slight to almost none, very short; under color light yellow 10–K–5, overtone deep yellow 3–A–12, overlaid on fruit which has been exposed to the sun for about half the surface with red streaks 8–J–6 to medium red 4–L–9 to light red 4–K–11.

Flesh: Color, yellow varying from light yellow 9–L–2 to darker overtones of yellow 9–L–7 and showing red 6–L–6 next to the stone; amygdalin, moderate; juice, moderate; texture, uniform through, firm to moderately soft but meaty when fully ripe; fibers, few, fine, tender; ripens, evenly; flavor, delicate, vinuous, aroma distinct; eating quality, best.

Stone: Completely free from the flesh; fibers, mostly short; size, medium to small, length average 1¼ inches, breadth average one inch, thickness average ⅝ inch; form, generally obovate to oval with small apical tip; base, generally straight; hilum, oval; apex, mucronate; sides, generally unequal, flattened on some on one side; surface, irregularly furrowed near base, and to some extent throughout, generally pitted toward base; pits, generally elongated; ventral edge, thicker than dorsal edge and furrowed throughout, with deeper furrows on the edges; dorsal edge, full, with deep groove from base to near apex; color, light brown 15–E–12 with dark brown spots 48–L–12.

Use: Local and long distance shipment.

Although the new variety of peach possesses the described characteristics under the growing conditions in Exeter, Tulare County, Calif., having first been observed near Red Bluff, Tehama County, Calif., it is to be understood that variation of the usual magnitude in characteristics incident to the growing conditions fertilization, pruning, and pest control is to be expected.

Having thus described and illustrated my new variety of peach tree, what is claimed is:

1. A new and distinct variety of peach substantially as illustrated and described and which is characterized by the very bright yellow undercolor of its skin, the very short and scant pubescence on the skin, its firmness of flesh, and its uniform texture of the flesh and resemblance to Improved Pacifica (U.S. Plant Patent No. 2,425) but distinguished therefrom primarily by the characteristics of being slightly later in ripening, having a brighter undercolor of the skin, and having flesh that is more uniformly firm in texture.

No references cited.

ROBERT E. BAGWILL, Primary Examiner